United States Patent
Jin et al.

(10) Patent No.: US 12,268,594 B2
(45) Date of Patent: Apr. 8, 2025

(54) SPLIT-TYPE PRECISELY ANCHORED INTERVENTIONAL MITRAL VALVE SYSTEM

(71) Applicants: BEIJING BALANCE MEDICAL TECHNOLOGY CO., LTD., Beijing (CN); WEST CHINA HOSPITAL OF SICHUAN UNIVERSITY, Chengdu (CN)

(72) Inventors: Lei Jin, Beijing (CN); Yingqiang Guo, Beijing (CN); Jia Wu, Beijing (CN); Liyan Li, Beijing (CN); Hong Mu, Beijing (CN); Kangjian Wu, Beijing (CN); Zhihao Fan, Beijing (CN)

(73) Assignees: BEIJING BALANCE MEDICAL TECHNOLOGY CO., LTD., Beijing (CN); WEST CHINA HOSPITAL OF SICHUAN UNIVERSITY, Chengdu (CN)

( * ) Notice: Subject to any disclaimer, the term of this patent is extended or adjusted under 35 U.S.C. 154(b) by 0 days.

(21) Appl. No.: 18/710,524

(22) PCT Filed: Nov. 17, 2022

(86) PCT No.: PCT/CN2022/132578
§ 371 (c)(1),
(2) Date: May 15, 2024

(87) PCT Pub. No.: WO2023/088369
PCT Pub. Date: May 25, 2023

(65) Prior Publication Data
US 2025/0009500 A1   Jan. 9, 2025

(30) Foreign Application Priority Data
Nov. 17, 2021   (CN) .......................... 202111361271.6

(51) Int. Cl.
*A61F 2/24*  (2006.01)

(52) U.S. Cl.
CPC .......... *A61F 2/2415* (2013.01); *A61F 2/2418* (2013.01); *A61F 2/2433* (2013.01);
(Continued)

(58) Field of Classification Search
CPC .... A61F 2/2418; A61F 2/2415; A61F 2/2433; A61F 2210/0014; A61F 2210/0076;
(Continued)

(56) References Cited

U.S. PATENT DOCUMENTS 10,441,421 B2 * 10/2019 Perszyk ................. A61F 2/2454
11,364,117 B2 *  6/2022 Dale ..................... A61F 2/2418
(Continued)

FOREIGN PATENT DOCUMENTS

CN      105101911 A      11/2015
CN      106132352 A      11/2016
(Continued)

OTHER PUBLICATIONS

English translation form 237search report. International Search Report of PCT/CN2022/132578 dated Feb. 8, 2023.*
(Continued)

*Primary Examiner* — Suzette J Gherbi
(74) *Attorney, Agent, or Firm* — Outlier Patent Attorneys, PLLC

(57) ABSTRACT

A split type precisely-anchorable transcatheter mitral valve system comprises a split transcatheter mitral valve anchoring stent (10) and a transcatheter artificial biological mitral valve (20), wherein the shape and structure of the transcatheter mitral valve anchoring stent (10) are matched with the mitral valve real structure after the patient image data is subjected to three-dimensional reconstruction, the transcath-
(Continued)

eter mitral valve anchoring stent (10) is firstly delivered to the mitral valve position of the patient to be released and deformed, and the transcatheter artificial biological mitral valve (20) is in personalized precise alignment and coaptation with tissues on the mitral valve position of the patient and under the petals; the transcatheter artificial biological mitral valve (20) is delivered into the transcatheter mitral valve anchoring stent (10) to be released, the transcatheter artificial biological mitral valve (20) is released and deformed and expanded to a functional state, the transcatheter mitral valve anchoring stent (10) is again deformed and combined with the expanded transcatheter artificial biological mitral valve (20), and meanwhile, the re-deformation of the transcatheter mitral valve anchoring stent (10) enables the mitral valve anchoring stent (10) to be anchored with the lower leaflet tissue in a preset combination. The split type accurately anchored transcatheter mitral valve system can realize accurate anchoring of transcatheter mitral valve personalized based on a system designed by three-dimensional reconstruction.

29 Claims, 13 Drawing Sheets

(52) U.S. Cl.
CPC ............... *A61F 2210/0014* (2013.01); *A61F 2210/0076* (2013.01); *A61F 2220/0008* (2013.01); *A61F 2220/0083* (2013.01); *A61F 2230/0093* (2013.01); *A61F 2240/004* (2013.01)

(58) Field of Classification Search
CPC ...... A61F 2220/0008; A61F 2220/0083; A61F 2230/0093
See application file for complete search history.

(56) References Cited

U.S. PATENT DOCUMENTS

| | | | |
|---|---|---|---|
| 11,382,750 B2* | 7/2022 | Perszyk | ................ A61F 2/2418 |
| 2009/0005863 A1 | 1/2009 | Goetz et al. | |
| 2010/0249894 A1 | 9/2010 | Oba et al. | |
| 2011/0218619 A1 | 9/2011 | Benichou et al. | |
| 2012/0022639 A1 | 1/2012 | Hacohen et al. | |
| 2012/0078353 A1 | 3/2012 | Quadri et al. | |
| 2015/0039082 A1 | 2/2015 | Keränen et al. | |
| 2016/0113766 A1 | 4/2016 | Ganesan et al. | |
| 2016/0303804 A1* | 10/2016 | Grbic | ..................... G06T 19/00 |
| 2016/0324633 A1 | 11/2016 | Gross et al. | |
| 2016/0367360 A1 | 12/2016 | Cartledge et al. | |
| 2017/0112622 A1* | 4/2017 | Li | ........................ A61F 2/2418 |
| 2018/0289484 A1 | 10/2018 | Kofidis et al. | |
| 2018/0296341 A1 | 10/2018 | Noe et al. | |
| 2018/0338832 A1 | 11/2018 | Ganesan et al. | |
| 2020/0085573 A1* | 3/2020 | Armer | ................... A61F 2/2418 |
| 2021/0113330 A1* | 4/2021 | Benichou | .............. A61F 2/2418 |
| 2021/0322103 A1* | 10/2021 | Mortier | ................... G16H 50/30 |
| 2023/0218389 A1* | 7/2023 | Yang | .................... A61F 2/2412 623/2.17 |

FOREIGN PATENT DOCUMENTS

| | | |
|---|---|---|
| CN | 107405194 A | 11/2017 |
| CN | 107468379 A | 12/2017 |
| CN | 107928841 A | 4/2018 |
| CN | 108578016 A | 9/2018 |
| CN | 109009569 A | 12/2018 |
| CN | 109069271 A | 12/2018 |
| CN | 109922756 A | 6/2019 |
| CN | 111110398 A | 5/2020 |
| CN | 112754731 A | 5/2021 |
| CN | 113456299 A | 10/2021 |
| WO | 2015092554 A2 | 6/2015 |
| WO | 2021211062 A1 | 10/2021 |

OTHER PUBLICATIONS

First office action of prior Chinese application No. 202211441591.7 dated Jun. 21, 2023.

First search report of prior Chinese application No. 202211441591. 7.

International Search Report of PCT/CN2022/132578 dated Feb. 8, 2023.

* cited by examiner

SPLIT-TYPE PRECISELY ANCHORED INTERVENTIONAL MITRAL VALVE SYSTEM

CROSS-REFERENCE TO RELATED APPLICATIONS

This application claims priority to International Application No. PCT/CN2022/132578, filed on Nov. 17, 2022, which claims the priority benefit of China Patent Application No. 202111361271.6, filed on Nov. 17, 2021. The contents of the above identified applications are incorporated herein by reference in their entirety.

TECHNICAL FIELD

The invention relates to an artificial biological heart valve, in particular to a split type precisely-anchorable transcatheter mitral valve system.

BACKGROUND ART

According to "China Cardiovascular Disease Report 2019", the number of patients with heart valve disease in China reached 36.3 million in 2019, wherein the mitral valve disease patient is the largest group in heart valve surgery, the mitral regurgitation (MR) alone accounted for 29.2%, with over 10 million MR patients, and the severe mitral regurgitation patient required to perform surgery is about 2 million. Among them, 40% of patients cannot tolerate surgical intervention due to their advanced age, poor heart function, and multiple organ dysfunction, and there are about 800,000 patients with severe mitral regurgitation who cannot undergo surgical treatment can only hope for interventional treatment of the mitral valve.

With the continuous improvement of clinical applications and products for transcatheter aortic valve, it has become increasingly mature. Due to its advantages of minimally invasive surgery, no need for extracorporeal circulation, and precise results in the short to medium term, it has been recognized as an effective treatment for high-risk patients with elderly or traditional surgical aortic valve replacement. However, due to the fact that the mitral valve serves as the intracavitary valve of the left heart, its asymmetric saddle shaped mitral valve ring, diverse and lesion leaflet structures (such as mitral stenosis or mitral regurgitation, and both), complex subvalvular tissue (including chordae tendineae and papillary muscles), adjacent left ventricular outflow tract, and significant deformation of the perivalvular and subvalvular space with each cardiac cycle, the complexity of these anatomical forms and structures makes it almost impossible to design an implanted artificial mitral valve based on the concept of radial support of the shape and/or perivalvular space like the aortic valve. Therefore, in the past decade, the development of transcatheter mitral valves has fallen far behind that of transcatheter aortic valves, which should be attributed to the need for updated design concepts in product structure and anchoring principles.

According to literature reports, there have been nearly 20 types of transcatheter mitral valve products developed since 2012, as shown in FIG. 1, among them, 9 have attempted to be implanted into the human body, as shown in FIG. 2, as of now, 4 have stopped research and development. Except for Abbott, Medtronic, and Edwards Lifesciences, which have continued to report on their respective interventional mitral valve products recently (FIG. 3A-D), there have been few further clinical studies on other transcatheter mitral valve products, and the development of the transcatheter mitral valve industry is in a bottleneck period that urgently needs to be overcome. The existing transcatheter mitral valve products, as well as patents for similar products that have been publicly disclosed, are designed with a single use catheter implantation and integrated valve structure, making it difficult to meet the personalized and complex lesion environment of mitral valve position.

SUMMARY

Unlike all previous designs of transcatheter mitral valve products, the present invention provides a design of a split type transcatheter mitral valve system. The meaning of split type refers to the product consisting of two parts: a transcatheter mitral valve anchoring stent and a transcatheter artificial biological mitral valve, the former is first delivered to the mitral valve position through a catheter for release, and then the latter is introduced and combined with the former at the lesion valve position through the assistance and deformation of the balloon expansion force, thereby achieving anchoring mainly relying on the lesion valve tissue itself.

Unlike all previously disclosed transcatheter mitral valve products, the transcatheter mitral valve system of the present invention consists of two parts: a transcatheter mitral valve anchoring stent and a transcatheter artificial biological mitral valve, and the core point of the invention is that the anchoring of the valve intervention and the support of the valve leaflet are divided into two independent structures, that is, the split transcatheter mitral valve anchoring stent is responsible for the anchoring of the transcatheter artificial biological mitral valve, and the transcatheter artificial biological mitral valve is transported into the anchoring stent like the transcatheter valve in valve, and is released and combined with the anchoring stent to achieve the intervention of the transcatheter artificial biological mitral valve.

The transcatheter mitral valve system of the present invention consists of two parts: a split transcatheter mitral valve anchoring stent and a split type precisely-anchorable transcatheter artificial biological mitral valve. One of the main contents of the invention is that the shape and structure of the transcatheter mitral valve anchoring stent have two different anchoring states, namely the first anchoring state after catheter release and the second anchoring state after combined with the interventional mitral valve.

The first anchoring state is designed based on the patient's personalized imaging data and three-dimensional reconstruction of the real structure and shape of the mitral valve, customized for in vitro three-dimensional shaping processing, and based on this, the deformation released by the catheter can be accurately aligned with the patient's mitral valve supravalvular and subvalvular tissue, the atrial surface to ventricular surface of the transcatheter mitral valve anchoring stent is funnel-shaped, and the deformation and return after release can accurately align with the dynamic lesion mitral valve supravalvular and subvalvular tissue of the patient, and forming mutual clamping with it. The processing and shaping of the first anchoring state of the transcatheter mitral valve anchoring stent depends on how to achieve the precise matching degree between the transcatheter mitral valve anchoring stent and the real anatomical structure of the patient's mitral valve. The real structure of the three-dimensional reconstruction is a digital image model or a three-dimensional printed simulation entity model; the real structure of the three-dimensional reconstruction is a three-dimensional dynamic image of a virtual simulation after digital conversion of CT, ultrasonic and nuclear magnetic integrated images, and a corresponding three-dimensional printing simulation entity model.

The first anchoring state of the transcatheter mitral valve anchoring stent, as described above, is based on the real anatomical shape of the patient's mitral valve reconstructed in three-dimension. It is specifically designed and processed into an umbrella shaped stent structure, which is composed of three parts: the atrial surface, the ventricular surface, and the anchoring stent connecting part therebetween. The ① atrial surface is an umbrella sheet, and has an umbrella shape matching with the real personalized morphology of the three-dimensional reconstruction of the image data of the atrial surface of the patient, that is the first lattice portion, and can be precisely laid on the bottom of the left atrium above the mitral annulus after release; the ② ventricular surface comprises two positioning hook loops which are precisely preset with the boundary positions of the anterior and posterior leaflets of the mitral valve of the patient; the ③ connecting part of the anchoring stent is in the shape of a circular funnel, which is the second grid part. At this point, the status of the transcatheter mitral valve anchoring stent after being completely released from the catheter is displayed. The first anchoring state of the connecting part of the transcatheter mitral valve anchoring stent is a three-dimensional shape-setting memory state of a real anatomical shape and a structure of the personalized corresponding patient after the catheter is delivered and released, the shape-setting memory state of the connecting part from the atrial surface to the ventricular surface has a contractional taper matched with the petal orifice to the subvalve, with the taper of 5-45 degrees, depending on the shape of the lesion leaflet of the patient; the connecting part of the anchoring stent is deformed to expand from the funnel-shaped deformation of the circular opening of the first anchoring state to the cylindrical preset second anchoring state. In the first anchoring state of the transcatheter mitral valve anchoring stent, after the positioning hook loop is released through the catheter, the anterior and posterior leaflet boundary positions of the lesion mitral valve of the patient matched with the positioning hook loop are accurately inserted, so as to realize personalized corresponding laying of the atrial surface of the positioning anchoring stent and the patient's left atrial morphology. The ventricular surface of the mitral valve anchoring stent has a plurality of anchoring hook loops, and the anchoring hook loops extend from the connecting part to the ventricular surface and then are folded, so as to accurately match the real chordae tendineae and subvalvular tissue structure morphology of the three-dimensional reconstruction of the patient's lesion mitral valve subvalvular imaging data. The number, size, morphology, and folding angle of the anchoring hook loops are accurately matched with the real chordae tendineae gap, the size and shape of the mitral valve leaflets, and the circumferential spacing of the perivalvular tissue from the ventricular wall in three-dimensional reconstruction.

The second anchoring state of the transcatheter mitral valve anchoring stent refers to the first anchoring state in which the transcatheter artificial mitral valve is catheterized into the transcatheter mitral valve anchoring stent in the first state, and then undergoes secondary deformation by balloon expandable external force, the conical funnel-shaped shape of the original first anchoring state is combined with the expanded interventional artificial mitral valve to form a final cylindrical shape, and meanwhile, the ventricular surface structure of the transcatheter mitral valve anchoring stent is finally combined with the patient's mitral valve tendon and papillary muscles to achieve anchoring, which is the second anchoring state of the transcatheter mitral valve anchoring stent.

The second anchoring state of the transcatheter mitral valve anchoring stent is mainly based on the patient's personalized three-dimensional reconstruction of mitral valve ultrasound images, including the shape and size of the mitral valve leaflets, the real anatomical structure of the tendon and papillary muscles beneath the leaflets, and the design and processing of the shape, size, and bending angle of the anchoring hook loop on the ventricular surface of the transcatheter mitral valve anchoring stent, so that when the transcatheter artificial mitral valve is inserted in a gripping state and can be expanded by pressurizing with a pump, an equal number of anchoring hook loops are matched in shape and structure, and the alignment deformation is the preset final anchoring state, and the final accurate and tight combination with the patient's mitral valve position and subvalvular tissue is achieved.

The transcatheter mitral valve anchoring stent is in a compressed state placed inside the catheter, and after being released through the catheter, it presents a first anchoring state, which is then combined with the transcatheter artificial biological mitral valve to transform into a second anchoring state, it is composed of several anchoring hook loops set by the connecting part of the anchoring stent to reconstruct the real anatomical shape of the patient's mitral valve based on personalized imaging data, and after being released through the catheter, it is accurately inserted into the two junctions of the anterior and posterior mitral valves to achieve the positioning of the entire stent. The anchoring hook loop not only locates the morphology of the atrial surface of the transcatheter mitral valve anchoring stent, the left atrium morphology of the patient and the amplitude of the left atrial systolic relaxation of the cardiac cycle, but also positions the anchoring hook loop of the ventricular surface of the transcatheter mitral valve anchoring stent to correspondingly insert, clamp and intervene the mitral valve anchoring stent into the second anchoring state, and the anchoring hook loops can be combined with the precise interlacing and tight presetting of the inferior valve tissue.

The transcatheter mitral valve anchoring stent is in a first anchoring state after being released by a catheter and then deformed into a second anchoring state in combination with a transcatheter artificial biological mitral valve, the atrial surface end portion of the connecting part of the transcatheter mitral valve anchoring stent is provided with a plurality of fixed support rod for embedding a transcatheter artificial biological mitral valve stent, and the fixed support rods are bent along the axial direction of the atrial surface and the ends thereof bend toward the axis of the anchoring stent; the connecting part of the mitral valve anchoring stent is provided with a plurality of end centripetal hook loops for embedding the outflow end of the transcatheter artificial biological mitral valve stent, and the atrial surface end portions of the connecting parts of the centripetal hook loops and the mitral valve anchoring stent are provided with a plurality of fixed support rod for embedding the atrial end of the transcatheter artificial biological mitral valve stent in an up-and-down closure, which can prevent displacement to the ventricular side during the release of the transcatheter artificial biological mitral valve. In the first anchoring state of the transcatheter mitral valve anchoring stent, the fixed support rod maintains an angle consistent with the connecting part of the anchoring stent, and in the second anchoring state of the mitral valve anchoring stent, the plurality of fixed support rod are axially parallel to the coaptation circumference, so that the end of the fixed support rod is embedded on the stent of the inflow end of the transcatheter artificial biological mitral valve, and fixed transcatheter artificial biological mitral valve ensures zero displacement of transcatheter artificial biological mitral valve release.

The first lattice portion and the second lattice portion of the transcatheter mitral valve anchoring stent are formed of a unit lattice composed of a compressible diamond lattice, a V-shaped lattice and/or a hexagonal or polygonal lattice, and the first lattice portion is adaptively connected to the second lattice portion.

An outer periphery of the lattice portion of the atrial surface of the transcatheter mitral valve anchoring stent is spaced apart from the atrial wall of the patient by 1-2 mm, preferably by 1.5 mm. An inner peripheral edge diameter of the second lattice portion of the transcatheter mitral valve anchoring stent matches an outer diameter of various corresponding size specifications of the transcatheter artificial biological mitral valve. A surface of the transcatheter mitral valve anchoring stent is coated with a layer of medical polymer film. The connecting parts of the atrial surface, the ventricular surface and the anchoring stent of the mitral valve anchoring stent are formed by machining the connecting parts of the three-dimensional forming structure or the atrial surface, the ventricular surface, and the anchoring stent after laser integrated cutting. The anchoring stent is a metallic material or a non-metallic material having shape memory reshape properties. The anchoring stent is made of a nickel-titanium alloy material. The transcatheter artificial biological mitral valve comprises a radially compressible stent, a cobalt-chromium alloy stent with a cylindrical shape or a partially cylindrical shape after being expanded by the balloon, or a radially compressible self-expanding nitinol stent, and three fan-shaped leaflets disposed on the inner side of the stent, each of the fan-shaped leaflets has a free edge, an arc-shaped bottom edge, and leaflet boundary connecting parts extending on both sides, and the stent is a metal net tube or a valve stent capable of supporting three types of crimped valve stents fixed at an interface of three pairs of leaflets. The valve stent is a cobalt-based alloy cobalt or chromium alloy or a nickel-titanium alloy. The transcatheter artificial biological mitral valve delivery kit comprises a transcatheter artificial biological mitral valve delivery device, a guide sheath, a valve holder, and a charging pump. The transcatheter mitral valve anchoring stent delivery device and the transcatheter artificial biological mitral valve delivery device can be punctured via femoral vein puncture, apical puncture, or left atrium puncture. The transcatheter mitral valve anchoring stent is firstly divided into a split type accurately anchoring lesion mitral valve position and releasing the same into a first anchoring state, and then the transcatheter artificial biological mitral valve is sent to the anchoring stent through a catheter, and as the transcatheter artificial biological mitral valve is expanded, the transcatheter mitral valve anchoring stent is expanded to a second anchoring state, and finally, the fitting of the stent binding portion and the transcatheter artificial biological mitral valve and the stent ventricular surface finish further tight binding with the inferior valvular structure to form final anchoring. Each completion of the transcatheter artificial biological mitral valve treatment process accurately anchored for the personalized preset realization of a specific patient, all the related data is used as an independent data unit to accumulate a large amount of personalized data, and the intelligent, large-scale and industrialization of the split type precisely-anchorable transcatheter mitral valve system mitral valve system is realized through artificial intelligence.

DETAILED DESCRIPTION

By combining the accompanying drawings and the specific description of the present invention mentioned above, it is possible to have a clearer understanding of the details of the present invention. However, the specific embodiments of the present invention described herein are only for the purpose of explaining the present invention and cannot be understood in any way as a limitation of the present invention. Under the guidance of the present invention, technicians may conceive any possible variations based on the present invention, which should be considered within the scope of the present invention.

According to the present invention, a split type precisely anchored transcatheter mitral valve system comprises a split transcatheter mitral valve anchoring stent 10 and a transcatheter artificial biological mitral valve 20, wherein the shape and structure of the transcatheter mitral valve anchoring stent are matched with the anatomical structure of the mitral valve real lesion after the patient image data is subjected to three-dimensional reconstruction, the transcatheter mitral valve anchoring stent is firstly delivered to the mitral valve site of the patient lesion through a catheter to be released, deformed and aligned with the mitral valve supravalvular and subvalvular tissue of the patient; the transcatheter artificial biological mitral valve is delivered into the transcatheter mitral valve anchoring stent which has been aligned and engaged with the tissue through a catheter, the transcatheter artificial biological mitral valve is released and deformed and expanded to a functional state, the transcatheter mitral valve anchoring stent is again deformed and combined with the expanded transcatheter artificial biological mitral valve, and meanwhile, the re-deformation of the transcatheter mitral valve anchoring stent enables the rebinding of the anchoring stent and the lesion mitral valve and subvalvular tissue to achieve final anchoring of the transcatheter artificial biological mitral valve. Since the real lesion of each patient is different, the transcatheter mitral valve anchoring stent designed according to the image data of the patient through three-dimensional reconstruction is also not the same, it will be adjusted according to the real situation of the patient, as shown in FIGS. 4A-D, it is a combined schematic diagram of the split type anchoring stent and the transcatheter artificial biological mitral valve with different supravalvular and subvalvular structures on the four types, but the general structure and constitution are based on the same design concept and concept.

Figure 1:
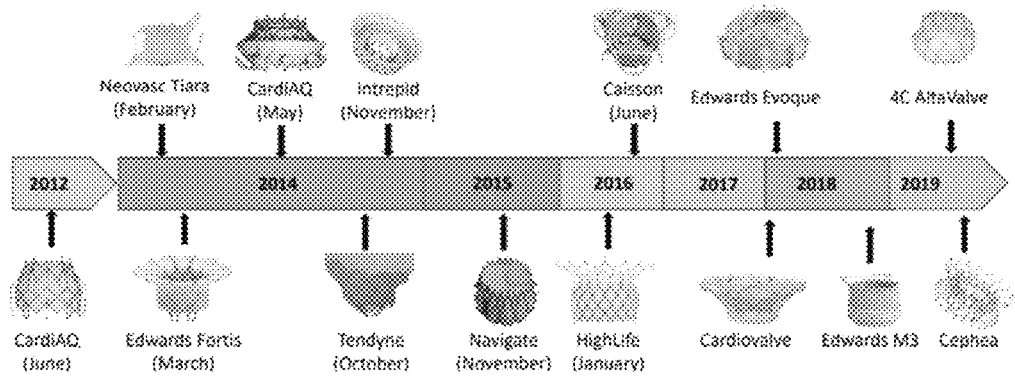
FIG. 1 shows a physical image of various transcatheter artificial biological mitral valves in 2012-2019.
Figure 2:
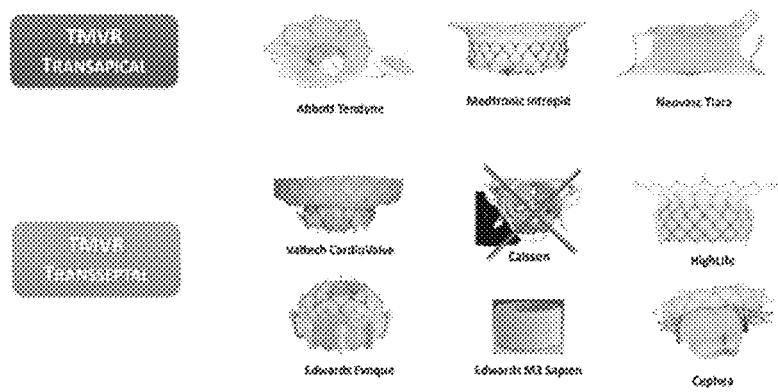
FIG. 2 shows a physical image of a transcatheter artificial biological mitral valve implanted through a human body in the prior art.
Figure 3A:
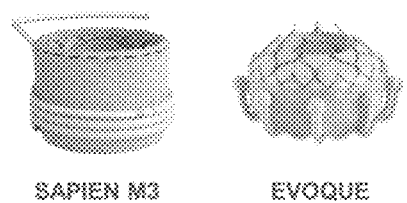
FIGS. 3A-3C show a physical image of a transcatheter artificial biological mitral valve currently in development.
Figure 3B:
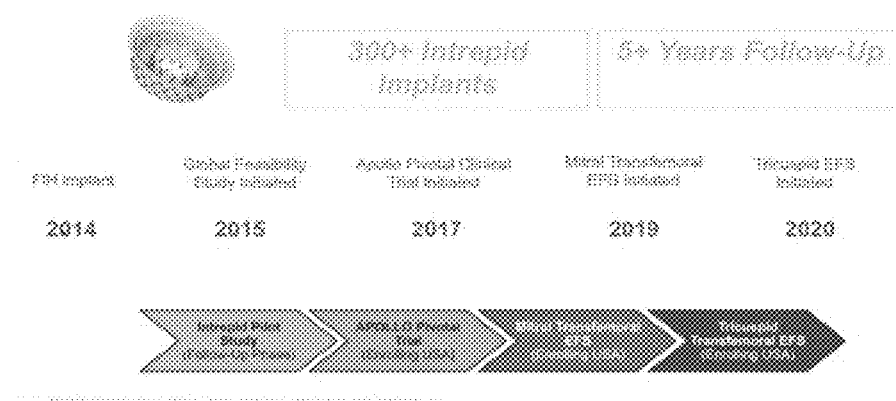
Figure 3C:
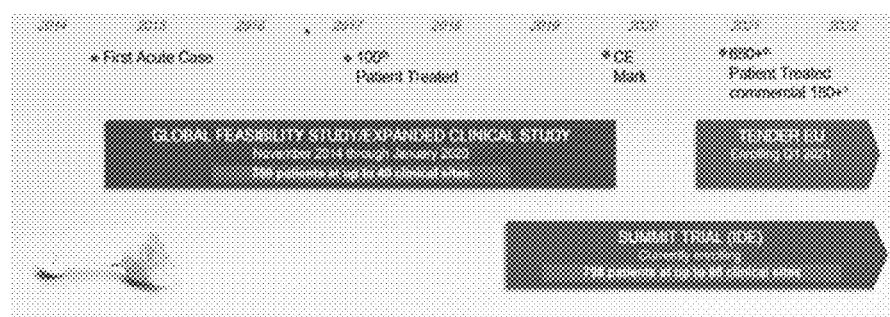
Figure 4A:
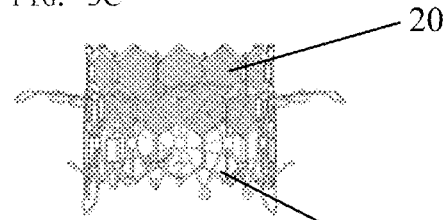
FIG. 4A-4D show schematic diagram of a combination of a split type anchoring stent and a transcatheter artificial biological mitral valve with different supravalvular and subvalvular structures according to an embodiment of the present invention.
Figure 4B:
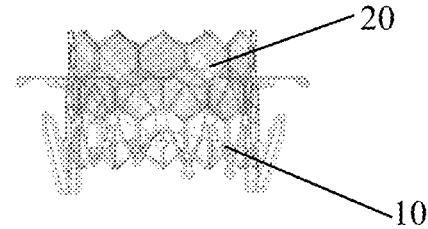
Figure 4C:
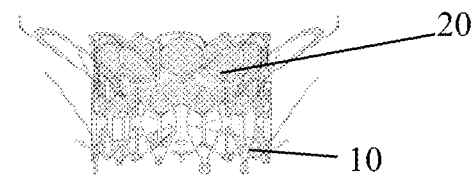
Figure 4D:
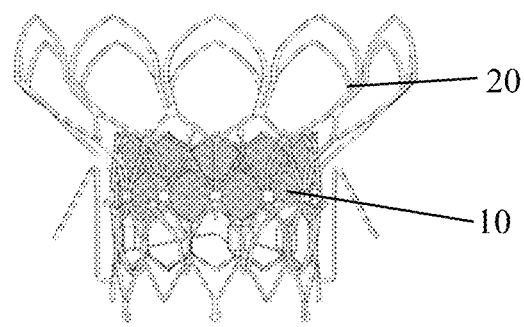
Figure 5A:
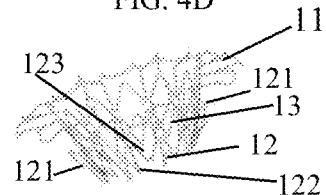
FIG. 5A-5D show a schematic diagram of a split type anchoring stent with different supravalvular and subvalvular structures according to an embodiment of the present invention.
Figure 5B:
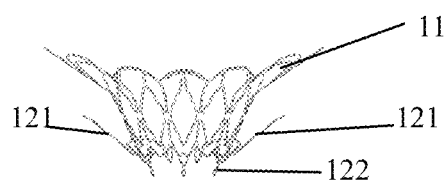
Figure 5C:
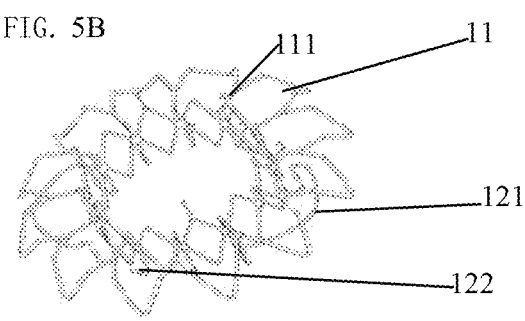
Figure 5D:
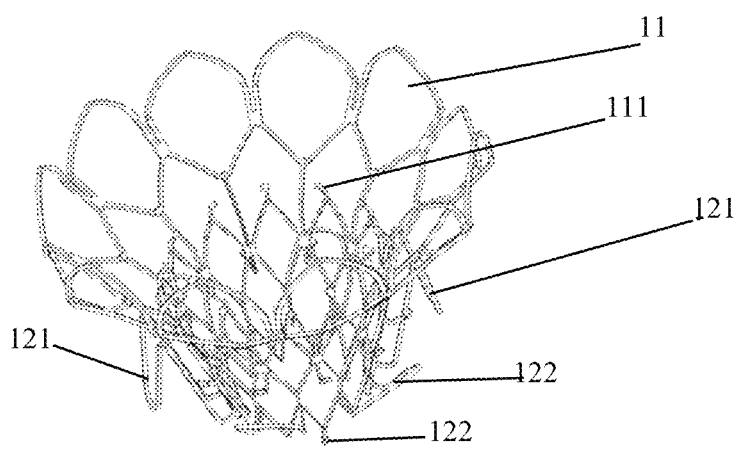
Figure 6:
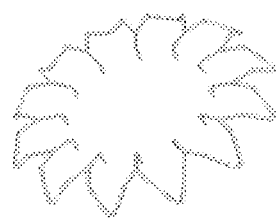
FIG. 6 shows a schematic diagram of an atrial surface of a split type anchoring stent according to an embodiment of the present invention.
Figure 7:
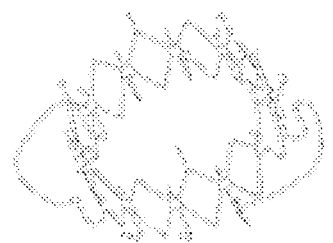
FIG. 7 shows a schematic diagram of a ventricular surface and a stent connecting part of a split type anchoring stent according to an embodiment of the present invention.

As shown in FIGS. 5-7, according to the present application, the transcatheter mitral valve anchoring stent 10 is shaped like a funnel-shaped stent structure shaped as an atrial surface large ventricular surface, is an umbrella tubular stent structure, comprising an atrial surface 11, a ventricular surface 12 and an anchoring stent connecting part 13 therebetween, wherein the atrial surface is an umbrella sheet with an umbrella shape matched with a real form of three-dimensional reconstruction of left atrium surface image data of a patient, that is, a first lattice portion; the ventricular surface 12 is a plurality of positioning hook loops 121 and anchoring hook loops 122 matched with a real shape of three-dimensional reconstruction of image data of a patient lesion mitral valve annulus; the anchoring stent connecting part 13 is a small circular opening funnel-shaped structure from an atrium surface to a ventricular surface, the length of the connecting part is matched with the corresponding transcatheter artificial biological mitral valve height, and has a second lattice portion 123 which can be expanded into a cylindrical shape. As shown in FIGS. 5A-5C, the schematic diagram of the split type anchoring stent with different upper leaflet infrastructures is consistent, but due to matching patient tissues of different patients, the atrial surface 11, the positioning hook loop 121, and the number, angle, length, and the like of the anchoring hook loop 122 of different degrees of curvature are designed. In other words, the shape of the atrial surface of the transcatheter mitral valve anchoring stent, the size of the covering area, the shape, the number, the length, the angle and the structural relationship of the ventricular surface of the stent and the anchoring hook loop are all according to the pre-operative CT image data of the individual of the patient, the real structures of the atrium (supravalvular) 40 and the ventricle (subvalvular) 50 of the patient after three-dimensional reconstruction (3mensio) and the respective diameter limiting structures measured by the reference three-dimensional ultrasonic image correspond to the real size, so that the processing drawing of the transcatheter mitral valve anchoring stent is designed, and the personalized mitral valve anchoring stent is finally prepared by three-dimensional laser cutting and three-dimensional forming processing of the specific nickel-titanium memory alloy tube.

Figure 8A:
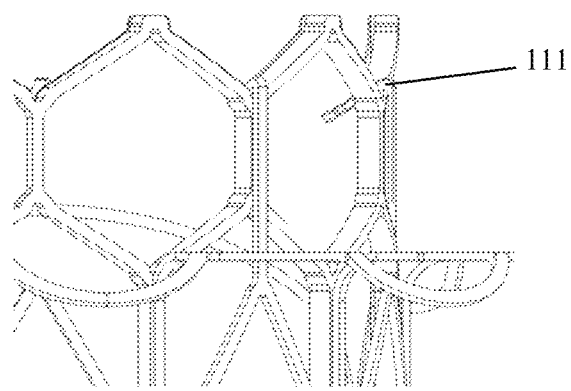
FIGS. 8A-C show a schematic diagram of fixed support rods and centripetal bending of a split type anchoring stent according to an embodiment of the present invention.
Figure 8B:
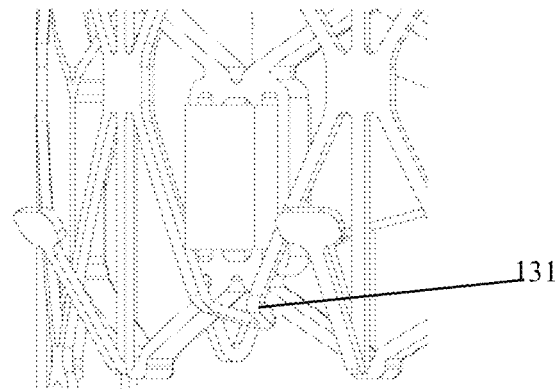
Figure 8C:
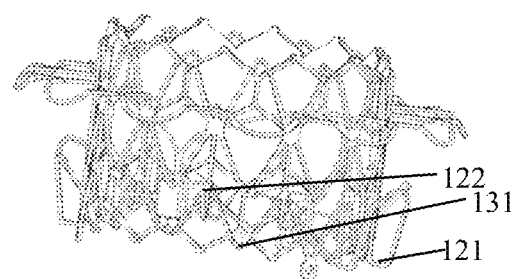

Referring to FIGS. 8A-8C, in order to make the combination of the anchoring stent and the transcatheter artificial biological mitral valve more firm, the end portion of the atrial surface 11 of the connecting part of the transcatheter mitral valve anchoring stent is provided with a plurality of fixed support rod 111 for embedding the transcatheter artificial biological mitral valve stent, and the fixed support rods are bent along the axial direction of the atrial surface and the ends thereof bend toward the axis of the anchoring stent. Alternatively, the connecting part of the mitral valve anchoring stent is provided with a plurality of end centripetal hook loops 112 for embedding the outflow end of the transcatheter artificial biological mitral valve stent. In the first anchoring state of the transcatheter mitral valve anchoring stent, the fixed support rod 111 maintains an angle consistent with the anchoring stent connecting part, and in the second anchoring state of the mitral valve anchoring stent, the plurality of fixed support rod 111 are axially parallel to the coaptation circumference, so that the end of the fixed support rod is embedded on the stent of the inflow end of the transcatheter artificial biological mitral valve, and the transcatheter artificial biological mitral valve is fixed to prevent displacement to the atrial surface. The fixed support rod 111 is 3-12.

The first lattice portion and the second lattice portion of the transcatheter artificial biological mitral valve anchoring stent are formed of a unit lattice composed of a compressible diamond lattice, a V-shaped lattice and/or a hexagonal or polygonal lattice, and the first lattice portion is adaptively connected to the second lattice portion. The outer periphery of the lattice portion of the atrial surface of the transcatheter mitral valve anchoring stent is spaced 1-2 mm from the atrial wall of the patient, preferably 1.5 mm apart. The inner peripheral diameter of the second lattice portion of the transcatheter mitral anchoring stent matches the outer diameters of the various respective size specifications of the transcatheter artificial biological mitral valve. A layer of medical polymer film is coated on the surface of the transcatheter mitral valve anchoring stent. The connecting part of the atrial surface, the ventricular surface and the anchoring stent of the mitral valve anchoring stent is a connecting part body processing and reconnecting structure of a three-dimensional forming structure or an atrial surface, a ventricular surface, and an anchoring stent after laser integrated cutting. The anchoring stent is a metal material or a non-metal material with shape memory reshape performance, for example, a nickel-titanium alloy material.

Figure 9A:
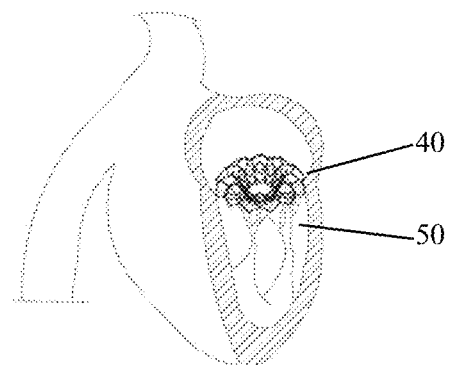
FIG. 9A-9C show a schematic diagram of a first anchoring state after a transcatheter mitral valve anchoring stent is implanted into a human body according to an embodiment of the present invention.
Figure 9B:
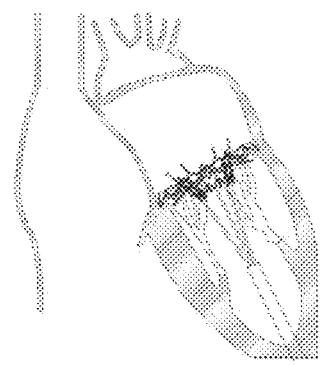
Figure 9C:
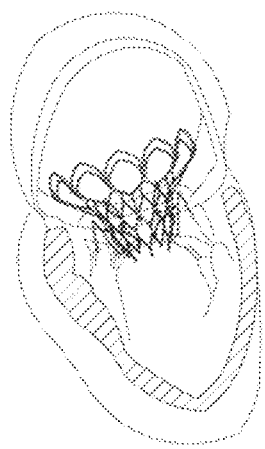
Figure 10A:
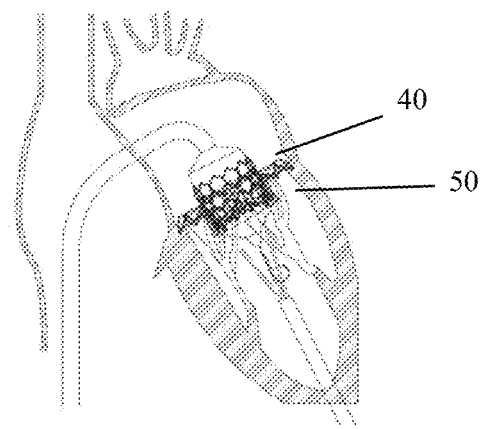
FIG. 10A-10C show a schematic diagram of a second anchoring state after a transcatheter mitral valve anchoring stent is implanted into a human body according to an embodiment of the present invention.
Figure 10B:
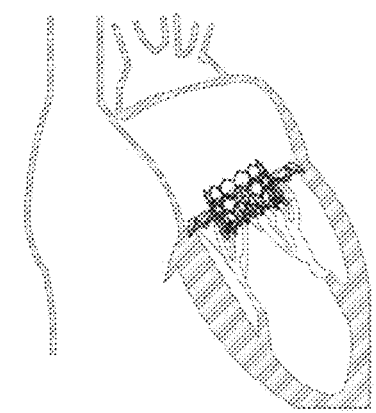
Figure 10C:
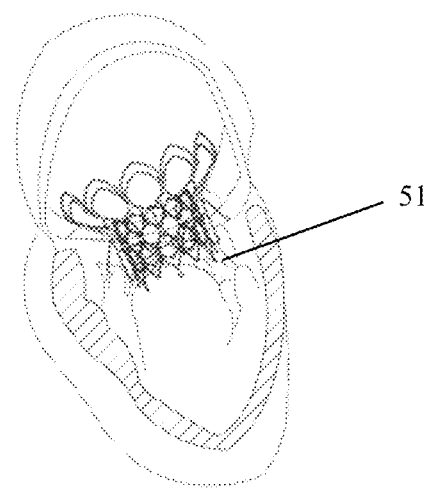
Figure 11:
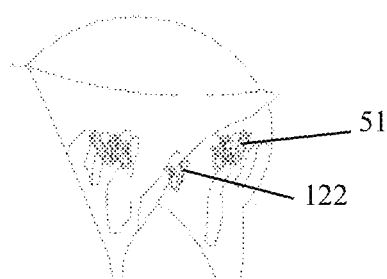
FIG. 11 shows a schematic diagram of anchoring hook loops and chordae tendineae secondary anchoring after a transcatheter mitral valve anchoring stent is implanted into a human body according to an embodiment of the present invention.

The above method for processing and manufacturing the mitral valve anchoring stent according to the real data of the personalized image of the patient is the pre-crimping state of the stent, or the stent is delivered by the catheter to the first anchoring state after the mitral valve is released at the lesion petal, as shown in FIGS. 9A-9C. The second anchoring state of the transcatheter mitral valve anchoring stent is that when the transcatheter artificial biological mitral valve is delivered into the anchoring stent via the catheter, by balloon assisted expansion, the transcatheter artificial biological mitral valve is expanded (or the nickel-titanium memory alloy transcatheter artificial biological mitral valve stent self-expands) to deform the mitral valve anchoring stent from the first anchoring state to the second anchoring state, and the deformation force of the stent is integrated with the ball expansion force released by the transcatheter artificial biological mitral valve as shown in FIGS. 10A-10C. Meanwhile, the anchoring hook loop of the ventricular surface of the anchoring stent, which is inserted into the subvalvular chordae tendineae and subvalvular tissue, is further tightly integrated with the chordae tendineae and subvalvular tissue 51 to achieve final anchoring as the anchoring stent deforms from the first anchoring state to the second anchoring state under the external force of the transcatheter balloon dilation, as shown in FIG. 11. At the same time, in the first anchoring state of the anchoring stent, the atrial end fixed support rods or stent bending of the connecting structure of the anchoring stent is deformed into the second anchoring state, and the anchoring stent is axially parallel to the encircling circumference, so that the fixed support rod end or stent bending and the connecting ventricular end of the stent hook loop force buckle onto the support rods at both ends of the transcatheter mitral valve stent, and the structure of the anchoring stent and the automatic kissing buckle at the two ends of the transcatheter artificial biological mitral valve stent enables the transcatheter artificial biological mitral valve and the anchoring stent to be accurately combined together, ensuring the zero displacement of the transcatheter artificial biological mitral valve, as shown in FIGS. 8A-8C.

The invention has the creative core point that: ① the anchoring stent and the transcatheter artificial biological mitral valve are independently formed in two independent form structures and can be combined with each other, the anchoring stent and the transcatheter artificial biological mitral valve are respectively delivered to the mitral valve position via a catheter, the anchoring stent is firstly engaged and clamped with the lesion valve through the structural design anchoring stent, and then the anchoring stent and the transcatheter artificial biological mitral valve are expanded and released and deformed and embedded into a whole; ② the anchoring stent and the lesion valve are engaged and clamped to be designed and processed according to the dynamic image data of the pre-operative personalized lesion mitral valve supravalvular and subvalvular structure of the patient and are three-dimensional shaped; ③ in order to ensure the connection and clamping between the anchoring stent and the lesion valve, the stent is designed with two positioning hook loops, and by utilizing the junction of the two leaflets of the mitral valve, the atrial surface shape similarity of the anchoring stent is accurately located, and the anchoring hook loop structure under the stent valve is aligned with the chordae tendineae and papillary muscles of the mitral valve leaflets in a numerical manner; ④ the first anchoring state (funnel-shaped) after the release of the anchoring stent is designed as a conical funnel-shaped shape based on the patient's personalized and real pathological anatomical structure, as a preset transition state for the second state (cylindrical), and then, with the help of the deformation force released by the transcatheter artificial biological mitral valve balloon dilation, the anchoring stent is deformed into a cylindrical second anchoring state, and the combined force of the deformation memory of nickel titanium alloy and the radial support force of the transcatheter artificial biological mitral valve stent causes the anchoring stent clamped supravalvular and subvalvular to deform into a cylindrical second anchoring state, and the subvalvular tissue is tightened again between the anchoring stent and the ventricular wall, completing the final anchoring; ⑤ the anchoring stent is deformed from the first state to the second state, the deformation process achieves automatic binding with the transcatheter artificial biological mitral valve, and the release manipulation of the transcatheter artificial biological mitral valve can be automatically and accurately achieved.

Figure 12A:
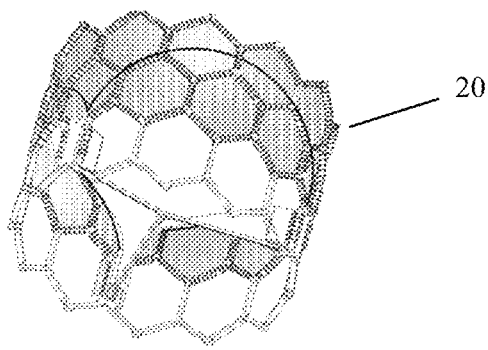
FIG. 12A-12B show a schematic diagram of a transcatheter artificial biological mitral valve before and after compression according to an embodiment of the present invention.
Figure 12B:
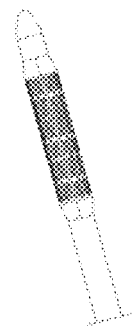
Figure 13:
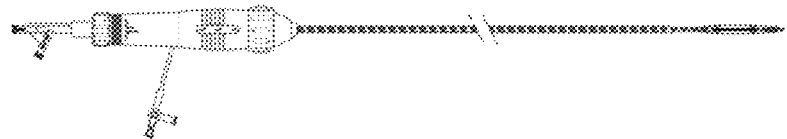
FIG. 13 shows a schematic diagram of a delivery system according to an embodiment of the present invention.

The transcatheter artificial biological mitral valve according to the present invention, due to the combination of the anchoring stent, the valve frame structure only serves the reasonable support of the three leaflets, including a radially compressible cobalt chromium alloy stent that can be cylindrical after balloon expansion, or a radially compressible nickel titanium alloy stent that can be cylindrical after self-expansion, and the three fan-shaped leaflets set on the inner side of the stent have free edges, curved bottom edges, and connecting parts extending on both sides of the leaflet junction, and the stent is a metal net tube or various forms of compressible valve stents that can support the fixation of the three leaflet junction. The valve frame is made of cobalt based alloy, cobalt or chromium alloy, or nickel titanium alloy. Please refer to FIGS. 12A-12B.

The split type precisely anchored transcatheter mitral valve system of the present invention further comprises a delivery assembly comprising a transcatheter mitral valve anchoring stent delivery kit and a transcatheter artificial biological mitral valve delivery kit 30, the transcatheter mitral valve anchoring stent delivery kit comprising a delivery catheter 31, a transcatheter mitral valve anchoring stent loader 32. The transcatheter artificial biological mitral valve delivery kit includes a transcatheter artificial biological mitral valve delivery device, a guide sheath, a valve holder, and a charging pump (all similar to the prior art, not explicitly shown). The transcatheter mitral valve anchoring stent delivery device and the transcatheter artificial biological mitral valve delivery device may be inserted through a femoral vein puncture, apical puncture, or left atrial puncture.

When using the split type precisely-anchorable transcatheter mitral valve system of the present invention for interventional treatment, can use the transapical approach or the transfemoral approach into the right atrium through atrial septum, or if necessary, both composite approaches can be simultaneously used.

Figure 14:
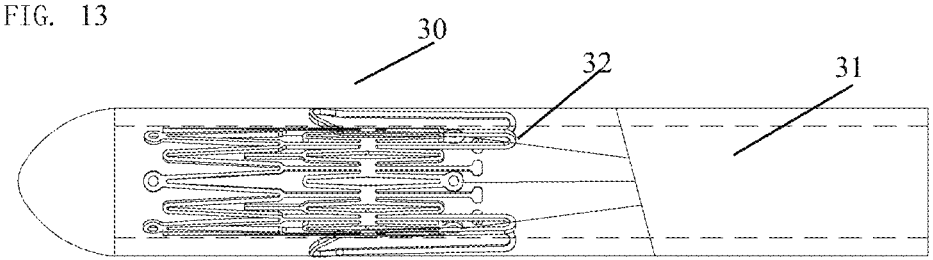
FIG. 14 shows a schematic diagram of a loading of a transcatheter mitral valve anchoring stent by a transapical approach.
Figure 15A:
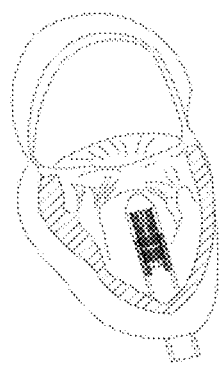
FIGS. 15A-E show schematic views of a process of a transcatheter mitral valve anchoring stent by a transapical approach.
Figure 15B:
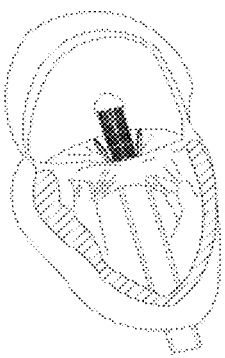
Figure 15C:
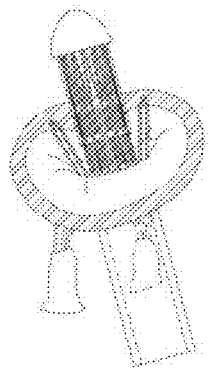
Figure 15D:
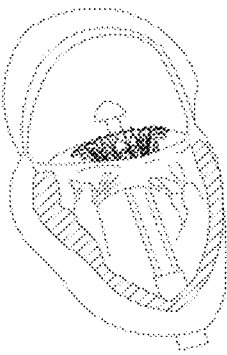
Figure 15E:
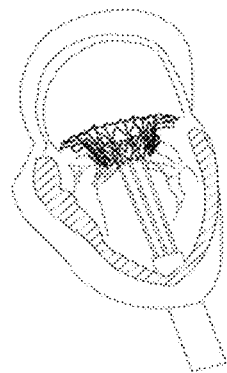
Figure 16A:
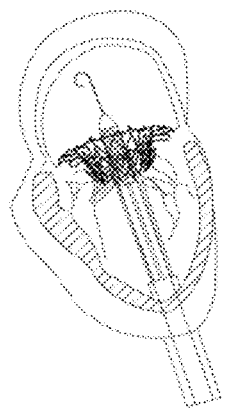
FIG. 16A-B show a schematic diagram of a process of a mitral valve anchoring stent by a transapical approach.

FIGS. 14-16 show the transapical approach.

Figure 16B:
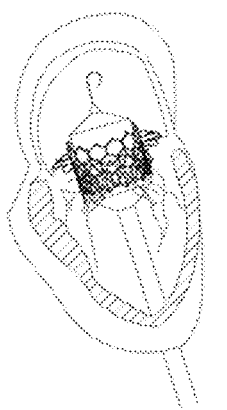

The transapical approach is often a familiar implementation method for cardiac surgeons. Firstly, the loaded anchoring stent is delivered into the mitral valve (FIG. 15A) of the lesion of the patient through the transapical approach, the positioning hook loop is released (FIG. 15B), and positioning is completed (FIG. 15C); the atrial surface (FIG. 15D), the stent connecting structure and the ventricular surface of the anchoring stent are released in sequence, and the ventricular surface anchoring hook loop is aligned and combined (FIG. 15E); the anchoring stent delivery device is withdrawn, the pre-loaded transcatheter artificial biological mitral valve is delivered to the anchoring stent original path along the original path, the pre-loaded transcatheter artificial biological mitral valve is delivered into the anchoring stent (FIG. 16A), then the transcatheter artificial biological mitral valve is expanded through balloon assistance, the anchoring stent is deformed into the second anchoring state, the anchoring stent is automatically and accurately combined with the transcatheter artificial biological mitral valve, and meanwhile, the anchoring stent is buckled with the inferior tissue to complete final anchoring (FIG. 16B).

Figure 17:
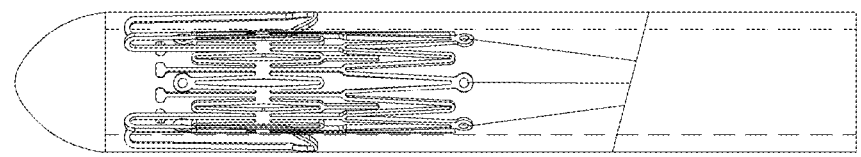
FIG. 17 shows a schematic diagram of a loading of a transcatheter mitral valve anchoring stent through atrial septum by a transfemoral approach according to an embodiment of the present invention.
Figure 18A:
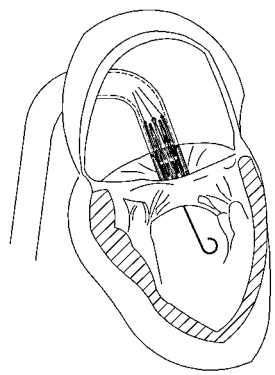
FIG. 18A-D show a schematic diagram of a process of a transcatheter mitral valve anchoring stent through atrial septum by a transfemoral approach according to an embodiment of the present invention.
Figure 18B:
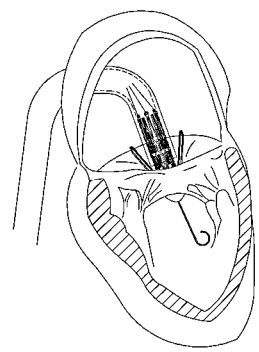
Figure 18C:
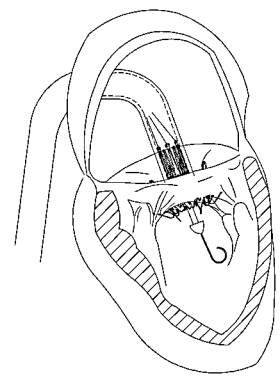
Figure 18D:
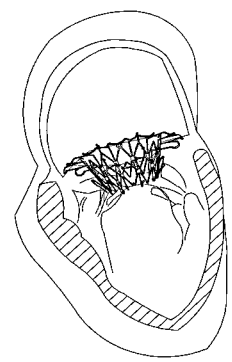
Figure 19A:
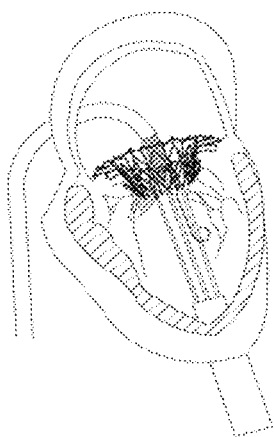
FIG. 19A-B show a schematic diagram of a process of feeding a transcatheter artificial biological mitral valve through atrial septum into an anchoring stent by a transfemoral approach according to an embodiment of the present invention.

FIGS. 17-19 show the transfemoral approach into the right atrium through atrial septum.

Figure 19B:
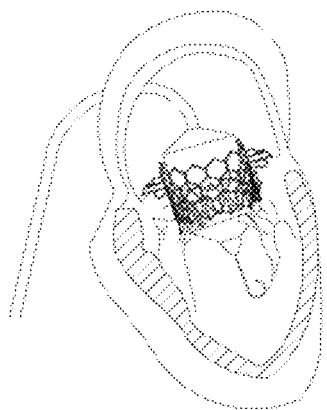

The transfemoral approach through atrial septum is a familiar implementation method for cardiologists. The loaded anchoring stent is transported through the interventricular septum via a venous route to the patient's lesion mitral valve (FIG. 18A), and the positioning hook loop is released to complete positioning (FIG. 18B), the anchoring stent is sequentially released on the ventricular surface (FIG. 18C), the stent connection structure, and the atrial surface, so that the anchoring hook loop on the ventricular surface is aligned and combined, which is the first anchoring state of the anchoring stent (FIG. 18C); the anchoring stent delivery device is withdrawn, the loaded transcatheter artificial biological mitral valve is delivered into the anchoring stent along the original path (FIG. 19A), then the transcatheter artificial biological mitral valve is expanded by balloon assistance, the anchoring stent is deformed into the second anchoring state, the anchoring stent is accurately combined with the transcatheter artificial biological mitral valve, and meanwhile, the anchoring stent is clamped with the subvalvular tissue to complete final anchoring (FIG. 19B).

Figure 20A:
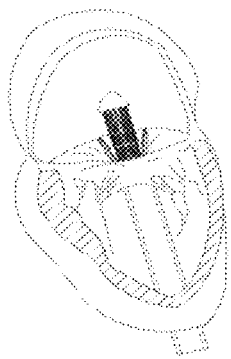
FIG. 20A-C show a schematic diagram of a process of introducing a composite approach into a transcatheter mitral valve anchoring stent according to an embodiment of the present invention.
Figure 20B:
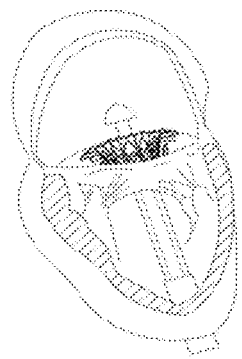
Figure 20C:
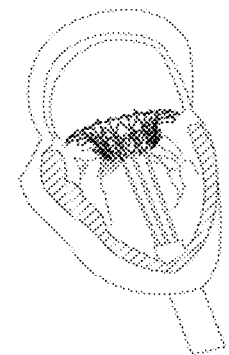

The transcatheter mitral valve system of the present invention is also shown in FIG. 20 through a composite approach.

Figure 21A:
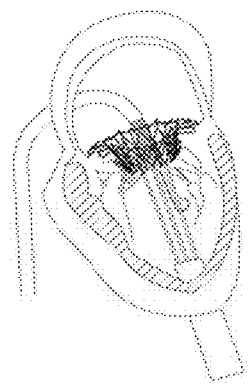
FIGS. 21A-D show schematic views of a process of feeding a transcatheter artificial biological mitral valve into an anchoring stent via a composite approach according to an embodiment of the present invention.
Figure 21B:
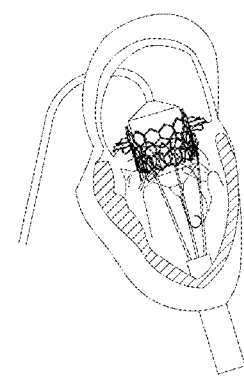
Figure 21C:
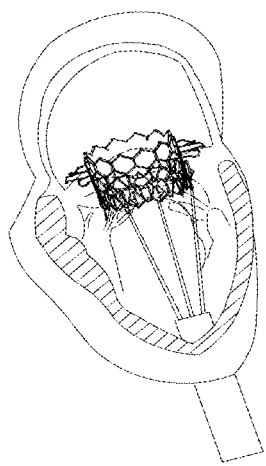
Figure 21D:
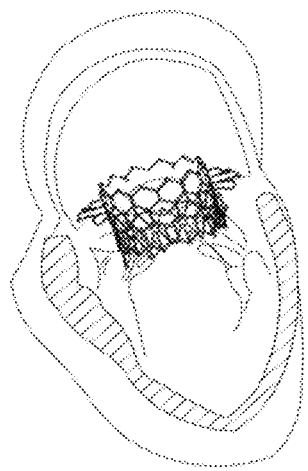

The composite approach is suitable for cases where preoperative imaging analysis of the heart structure is complex, and the first state anchoring alignment of the designed transcatheter anchoring stent is uncertain in terms of its firmness. Insert the loaded anchor stent into the patient's lesion mitral valve through the transapical approach, release the positioning hook loop for positioning (FIG. 20A), sequentially release the atrial surface and connecting part of the anchor stent (FIG. 20B), and then release the ventricular surface of the anchor stent to align the anchoring hook loop, which is the first state of the anchor stent (FIG. 20C), the anchoring stent delivery device is not withdrawn to pull the anchoring stent; then, the transcatheter artificial biological mitral valve loaded with the transcatheter artificial biological mitral valve is delivered into the anchoring stent through atrial septum at the same time, the transcatheter artificial biological mitral valve is expanded through balloon assistance, the anchoring stent is deformed into the second anchoring state, the anchoring stent is accurately combined with the transcatheter artificial biological mitral valve, and meanwhile, the anchoring stent is clamped with the inferior tissue to complete final anchoring (FIG. 21B); the transcatheter artificial biological mitral valve transporter (FIG. 21C) is withdrawn, the second anchoring state of the anchoring stent is confirmed to be in a designed state, and the anchoring stent delivery device is withdrawn after anchoring is firm (FIG. 21D).

The above embodiments are merely exemplary embodiments of the present invention.

The transcatheter mitral valve system of the present invention has performed the above technical solutions in animal experiments, and it has been confirmed that it is feasible.

The invention can realize the significance that: ① the split design realizes that the valve leaflet support and the valve anchoring are separated in function, the anchoring of the mitral valve position is delivered to the anchoring stent, so that the anchoring personalized design can be realized, and meanwhile, the anchoring stent and the transcatheter valve are inserted step by step, so that can avoid the difficulties in catheter delivery caused by the volume is too large after crimping; ② the anchoring principle and the pre-design and measurement of the final anchoring part are carried out through the anatomical structure characteristics of the lesion valve, and the second anchoring state of the anchoring stent is determined; the size and dimension of each part are constructed through the personalized image data of the patient, the special software and the three-dimensional printing pretest to complete the preset transition state, namely the three-dimensional shaping design and processing of the first anchoring state, so that the catheter is accurately aligned after being released, and the support is provided for smooth delivery of the transcatheter valve. For example, the conical structure of the first state of the anchoring stent can be moderately expanded and narrow, and can also be constrained more severely; the former not only provides a channel for valve intervention, but also can avoid sudden expansion of the stenotic lesion; the former can relieve a large amount of regurgitation of the valve insufficiency, and provides space and time guarantee for the entry of the transcatheter artificial biological mitral valve; ③ the external force released by the valve is used for driving the anchoring support to be deformed into a cylindrical second state from the funnel-like first anchoring state, and the deformation generates an anchoring stent centripetal gripping valve, so that the zero displacement of the valve is ensured by fitting with the transcatheter valve, and the anchoring hook loop structure is further tightly combined with the lower leaflet tissue by means of the ventricular surface anchoring hook loop structure, so that the pre-designed alignment anchoring is completed, and meanwhile, clamping is formed on the anchoring stent and the structure on the valve to achieve final anchoring; ④ the arrangement support rod structure of the inflow end and the outflow end of the connecting part of the transcatheter mitral valve anchoring stent can be integrated with the transcatheter artificial biological mitral valve from both ends to ensure that the valve is not displaced; ⑤ in the split type precisely-anchorable transcatheter mitral valve system described above, each completion of the transcatheter artificial biological mitral valve treatment process accurately anchored for the personalized preset realization, the analysis of related data, the shape design of the transcatheter mitral valve anchoring stent, processing and manufacturing, related data obtained in the whole process of interventional treatment and postoperative follow-up visit data and the like, as an independent data unit, a large amount of personalized image data, an anchoring stent design and related data such as processing and manufacturing parameters, a interventional treatment process and a postoperative result are accumulated, and the intelligent, commercialization and large-scale application of the interventional treatment implementation of the split type precisely-anchorable transcatheter mitral valve system is gradually realized.

The invention claimed is:

1. A split type precisely-anchorable transcatheter mitral valve system, characterized in that,
the system comprises a split transcatheter mitral valve anchoring stent and a transcatheter artificial biological mitral valve,
wherein the shape and structure of the transcatheter mitral valve anchoring stent are matched with the mitral valve real structure after patient image data is subjected to three-dimensional reconstruction, the transcatheter mitral valve anchoring stent is firstly delivered to the mitral valve position of the patient to be released, deformed, personalized and precisely aligned with the personalized precise alignment of the supravalvular and subvalvular tissues on the mitral valve position of the patient;
the transcatheter artificial biological mitral valve is delivered into the transcatheter mitral valve anchoring stent to be released, the transcatheter artificial biological mitral valve is released and deformed and expanded to a functional state, the transcatheter mitral valve anchoring stent is deformed again and combined with the expanded transcatheter artificial biological mitral valve, and meanwhile, the re-deformation of the transcatheter mitral valve anchoring stent causes the transcatheter mitral valve anchoring stent to be anchored with the subvalvular tissue in a preset combination;
the transcatheter mitral valve anchoring stent is an umbrella tubular stent structure, comprising an atrial surface, a ventricular surface and an anchoring stent connecting part therebetween, wherein the atrial surface is an umbrella sheet, and has an umbrella shape matching with a real personalized morphology of the three-dimensional reconstruction of the patient image data of the atrial surface of the patient, that is the first lattice portion; the ventricular surface comprises two positioning hook loops which are precisely preset with the boundary positions of the anterior and posterior leaflets of the mitral valve of the patient; the anchoring stent connecting part is funnel-shaped with a round opening, the diameter of the funnel opening is matched with the patient's mitral valve perivalvular inner diameter, and the opening of the lower end of the funnel is a second lattice portion that matches the morphology and degree of the mitral valve stenosis and/or regurgitation lesion.

2. The split type precisely-anchorable transcatheter mitral valve system according to claim 1, characterized in that, the mitral valve system further comprises a delivery assembly, the delivery assembly comprises a transcatheter mitral valve anchoring stent delivery set and a transcatheter artificial biological mitral valve delivery set, and the transcatheter mitral valve anchoring stent delivery set comprises a delivery catheter, a transcatheter mitral valve anchoring stent delivery device, and a stent loader.

3. The split type precisely-anchorable transcatheter mitral valve system according to claim 1, characterized in that, the split type transcatheter mitral valve anchoring stent and the transcatheter artificial biological mitral valve are in anterior and posterior routes, and then are assembled again into one body in vivo, and simultaneously the transcatheter mitral valve anchoring stent is deformed again to be combined with the mitral valve of the patient's lesion mitral valve and subvalvular tissue to achieve the mitral valve in situ replacement of the lesion mitral valve.

4. The split type precisely-anchorable transcatheter mitral valve system according to claim 1, characterized in that, the transcatheter mitral valve anchoring stent has a compressed state disposed in the catheter, a first anchoring state after being released by the catheter, and a second anchoring state after being combined with the transcatheter artificial biological mitral valve,
in the first anchoring state, the posterior deformation of the transcatheter mitral valve anchoring stent after being released by the catheter is in personalized precise alignment and engagement and clamping with the supravalvular and subvalvular tissue on the mitral valve position of the patient;
in the second anchoring state, the transcatheter artificial biological mitral valve is introduced into the transcatheter mitral valve anchoring stent in the first state by the catheter to expand the secondary deformation by balloon expandable external force, and it is integrated with the expanded transcatheter artificial biological mitral valve, and meanwhile, the transcatheter mitral valve anchoring stent is anchored with the patient's mitral valve position tissue in a preset combination.

5. The split type precisely-anchorable transcatheter mitral valve system according to claim 4, characterized in that,
in the first anchoring state, the transcatheter mitral valve anchoring stent is processed and shaped into a funnel shape with a large atrial surface and a small ventricular surface, the deformation and return of the transcatheter mitral valve anchoring stent after being inputted and released through a catheter accurately corresponds to the patient's dynamic lesion mitral valve supravalvular and subvalvular tissue, and the personalized alignment engagement and clamping is performed;
in the second anchoring state, the transcatheter mitral valve anchoring stent in the first anchoring state and the transcatheter artificial biological mitral valve in the transcatheter delivery stent are balloon expanded to integrate together, so that the transcatheter mitral valve anchoring stent is combined with the transcatheter artificial biological mitral valve by a centripetal return clamping generated by the secondary deformation from the original funnel shape to cylindrical shape, and meanwhile, the tight combination of the mitral valve position and the supravalvular tissue of the patient is completed.

6. The split type precisely-anchorable transcatheter mitral valve system according to claim 1, characterized in that, a real structure of the three-dimensional reconstruction is a digital image model or a three-dimensional printed simulation entity model; the real structure of the three-dimensional reconstruction is a three-dimensional dynamic image of a virtual simulation after digital conversion of CT, ultrasonic and nuclear magnetic integrated images and a corresponding three-dimensional printing simulation entity model.

7. The split type precisely-anchorable transcatheter mitral valve system according to claim 1, characterized in that, the first anchoring state of the anchoring stent connecting part is a three-dimensional shape-setting memory state of a real anatomical shape and a structure of the personalized corresponding patient after the catheter is delivered and released, the shape-setting memory state of the anchoring stent connecting part from the atrial surface to the ventricular surface has a contractional taper matched with the petal orifice to the subvalve, with the taper of 5-45 degrees, depending on the shape of the lesion leaflet of the patient; the anchoring stent connecting part is deformed to expand from the funnel-shaped deformation of the circular opening of the first anchoring state to the cylindrical preset second anchoring state.

8. The split type precisely-anchorable transcatheter mitral valve system according to claim 7, characterized in that, in the first anchoring state of the transcatheter mitral valve anchoring stent, after the positioning hook loop is released through the catheter, the anterior and posterior leaflet boundary positions of the lesion mitral valve of the patient matched with the positioning hook loop are accurately inserted, to position the atrial surface of the transcatheter mitral valve anchoring stent, so as to realize personalized corresponding laying with the patient's left atrial morphology.

9. The split type precisely-anchorable transcatheter mitral valve system according to claim 1, characterized in that, the ventricular surface of the transcatheter mitral valve anchoring stent has a plurality of anchoring hook loops, and the anchoring hook loops extend from the anchoring stent connecting part to the ventricular surface and then are folded, so as to accurately match the real chordae tendineae and subvalvular tissue structure morphology of the three-dimensional reconstruction of the patient's lesion mitral valve subvalvular imaging data.

10. The split type precisely-anchorable transcatheter mitral valve system according to claim 9, characterized in that, the number, size, morphology, and folding angle of the anchoring hook loops are accurately matched with the real chordae tendineae gap, the size and shape of the mitral valve leaflets, and the circumferential spacing of the perivalvular tissue from the ventricular wall in three-dimensional reconstruction.

11. The split type precisely-anchorable transcatheter mitral valve system according to claim 9, characterized in that, in the first anchoring state of the transcatheter mitral valve anchoring stent, after the anchoring hook loop is released through the catheter, the anchoring hook loop is positioned at the position of the chordae tendineae of the patient and the chordae tendineae gap position to engage in a numerical a numerical alignment; in the second anchoring state of the transcatheter mitral valve anchoring stent, a plurality of the anchoring hook loops form the clamping portion by the action of deformation and the resultant force of the atrial surface of the transcatheter mitral valve anchoring stent and the anchoring stent connecting part, and a plurality of deformed anchoring hook loops and the chordae tendineae under the patient's lesion mitral valve leaflet and the subvalvular tissue are tightly combined through a preset interwoven.

12. The split type precisely-anchorable transcatheter mitral valve system according to claim 9, characterized in that, the anchoring hook loop is 3-9.

13. The split type precisely-anchorable transcatheter mitral valve system according to claim 1, characterized in that, the atrial surface end portion of the anchoring stent connecting part of the transcatheter mitral valve anchoring stent is provided with a plurality of fixed support rod for embedding a stent of a transcatheter artificial biological mitral valve, and the fixed support rods are bent along the axial direction of the atrial surface and the ends thereof bend toward the axis of the anchoring stent.

14. The split type precisely-anchorable transcatheter mitral valve system according to claim 13, characterized in that, the anchoring stent connecting part of the mitral valve anchoring stent is provided with a plurality of end centripetal hook loops for embedding some ends of the outflow end of the stent of a transcatheter artificial biological mitral valve, and the centripetal hook loops and the plurality of fixed support rod are in an up-and-down closure, and structurally firmly integrated with the transcatheter mitral valve, and structurally firmly integrated with the transcatheter artificial biological mitral valve, thereby realizing zero displacement of the release of the transcatheter artificial biological mitral valve.

15. The split type precisely-anchorable transcatheter mitral valve system according to claim 13, characterized in that, in the first anchoring state of the transcatheter mitral valve anchoring stent, the plurality of fixed support rod maintains an angle consistent with the anchoring stent connecting part, and in the second anchoring state of the mitral valve anchoring stent, the plurality of fixed support rod are axially parallel to the coaptation circumference, so that the end of the fixed support rod is embedded on the inflow end of the stent of the transcatheter artificial biological mitral valve, and structurally firmly integrated with the transcatheter artificial biological mitral valve, thereby realizing zero displacement of the release of the transcatheter artificial biological mitral valve.

16. The split type precisely-anchorable transcatheter mitral valve system according to claim 13, characterized in that, the fixed support rod is 3-12.

17. The split type precisely-anchorable transcatheter mitral valve system according to claim 1, characterized in that, the first lattice portion and the second lattice portion of the transcatheter mitral valve anchoring stent comprise a compressible diamond lattice, a V-shaped lattice and/or a hexagonal lattice, and the first lattice portion is adaptively connected to the second lattice portion.

18. The split type precisely-anchorable transcatheter mitral valve system according to claim 1, characterized in that, an outer periphery of the lattice portion of the atrial surface of the transcatheter mitral valve anchoring stent is spaced apart from the atrial wall of the patient by 1-2 mm.

19. The split type precisely-anchorable transcatheter mitral valve system according to claim 1, characterized in that, an inner peripheral edge diameter of the second lattice portion of the transcatheter mitral valve anchoring stent matches an outer diameter of various corresponding size specifications of the transcatheter artificial biological mitral valve.

20. The split type precisely-anchorable transcatheter mitral valve system according to claim 1, characterized in that, a surface of the transcatheter mitral valve anchoring stent is coated with a layer of medical polymer film.

21. The split type precisely-anchorable transcatheter mitral valve system according to claim 1, characterized in that, the atrial surface, the ventricular surface, and the anchoring stent connecting part of the transcatheter mitral valve anchoring stent are formed by machining the connecting parts of the three-dimensional forming structure, or the atrial surface, the ventricular surface, and the anchoring stent after laser integrated cutting.

22. The split type precisely-anchorable transcatheter mitral valve system according to claim 1, characterized in that, the transcatheter mitral valve anchoring stent is a metallic material or a non-metallic material having shape memory reshape properties.

23. The split type precisely-anchorable transcatheter mitral valve system according to claim 1, characterized in that, the transcatheter mitral valve anchoring stent is made of a nickel-titanium alloy material.

24. The split type precisely-anchorable transcatheter mitral valve system according to claim 1, characterized in that, the transcatheter artificial biological mitral valve comprises a radially compressible stent, a cobalt-chromium alloy stent with a cylindrical shape or a partially cylindrical shape after being expanded by the balloon, or a radially compressible self-expanding nickel-titanium alloy stent, and three fan-shaped leaflets disposed on the inner side of the cobalt-chromium alloy stent or the nickel-titanium alloy stent, each of the fan-shaped leaflets has a free edge, an arc-shaped bottom edge, and leaflet boundary connecting parts extending on both sides, and the cobalt-chromium alloy stent or the nickel-titanium alloy stent is a valve stent capable of supporting three types of crimped valve stents fixed at an interface of three pairs of leaflets.

25. The split type precisely-anchorable transcatheter mitral valve system according to claim 1, characterized in that, the stent of the artificial biological mitral valve is made from material of cobalt-based alloy or chromium alloy or nickel-titanium alloy.

26. The split type precisely-anchorable transcatheter mitral valve system according to claim 2, characterized in that, the transcatheter artificial biological mitral valve delivery set comprises a transcatheter artificial biological mitral valve delivery device, a guide sheath, a valve holder, and a charging pump.

27. The split type precisely-anchorable transcatheter mitral valve system according to claim 26, characterized in that, the transcatheter mitral valve anchoring stent delivery device and the transcatheter artificial biological mitral valve delivery device can be punctured via femoral vein puncture, apical puncture, or left atrium puncture.

28. The split type precisely-anchorable transcatheter mitral valve system according to claim 24, characterized in that, the transcatheter mitral valve anchoring stent is firstly divided into a split type accurately anchoring lesion mitral valve position and releasing the same into a first anchoring state, and then the transcatheter artificial biological mitral valve is sent to the transcatheter mitral valve anchoring stent through a catheter, and as the transcatheter artificial biological mitral valve is expanded, the transcatheter mitral valve anchoring stent is expanded to a second anchoring state, and finally, a final anchoring is further formed by embedding the anchoring stent connecting part with the transcatheter artificial biological mitral valve and tightly binding the ventricular surface of the anchoring stent with the valvular tissue at the same time.

29. The split type precisely-anchorable transcatheter mitral valve system according to claim 1, characterized in that, each completion of the transcatheter mitral valve treatment process accurately anchored for the personalized preset realization of a specific patient, all of the related data of personalized mitral valve system is used as an independent data unit to accumulate a large amount of personalized data, and the intelligent, large-scale and industrialization of the split type precisely-anchorable transcatheter mitral valve system mitral valve system is realized through artificial intelligence.

* * * * *